(12) United States Patent
Kumar et al.

(10) Patent No.: US 8,043,382 B2
(45) Date of Patent: Oct. 25, 2011

(54) REINFORCED MEDICAL IMPLANTS

(75) Inventors: Mukesh Kumar, Warsaw, IN (US); James B. Fleming, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 106 days.

(21) Appl. No.: 11/712,360

(22) Filed: Feb. 28, 2007

(65) Prior Publication Data
US 2008/0208353 A1 Aug. 28, 2008

(51) Int. Cl.
*A61F 2/28* (2006.01)
(52) U.S. Cl. .................. 623/23.56; 623/23.54
(58) Field of Classification Search ............... 623/16.11, 623/23.5–23.56
See application file for complete search history.

(56) References Cited

U.S. PATENT DOCUMENTS

| | | | |
|---|---|---|---|
| 4,321,042 A | 3/1982 | Scheicher | |
| 4,813,959 A * | 3/1989 | Cremascoli | 623/22.27 |
| 4,813,960 A * | 3/1989 | Muller | 623/22.33 |
| 4,936,852 A * | 6/1990 | Kent et al. | 623/17.17 |
| 5,167,271 A | 12/1992 | Lange et al. | |
| 5,236,458 A | 8/1993 | Ducheyne et al. | |
| 5,944,759 A * | 8/1999 | Link | 623/18.11 |
| 5,984,968 A * | 11/1999 | Park | 623/16.11 |
| 6,102,954 A * | 8/2000 | Albrektsson et al. | 623/20.32 |
| 6,180,606 B1 | 1/2001 | Chen et al. | |
| 6,881,229 B2 | 4/2005 | Khandkar et al. | |
| 7,025,824 B2 * | 4/2006 | Axen et al. | 106/695 |
| 2003/0167093 A1 | 9/2003 | Xu et al. | |
| 2004/0243241 A1 | 12/2004 | Istephanous et al. | |
| 2005/0100726 A1 | 5/2005 | Millard et al. | |

FOREIGN PATENT DOCUMENTS

| | | |
|---|---|---|
| CH | 586166 | 3/1977 |
| WO | WO 01/68004 | 9/2001 |

OTHER PUBLICATIONS

McGraw-Hill Encyclopedia of Science and Technology, 9th Edition, vol. 3: BIO-CHA. McGraw-Hill, New York, 2002. pp. 704-710.
Engineered Materials Handbook, vol. 1: Composites. ASM International, Metals Park, Ohio, 1987. pp. 925-932.

* cited by examiner

*Primary Examiner* — David Isabella
*Assistant Examiner* — Yashita Sharma
(74) *Attorney, Agent, or Firm* — Harness, Dickey

(57) ABSTRACT

Medical implants having a ceramic body reinforced with a plurality of metal wires. Methods of making the implant and methods of implanting the medical implant are also provided.

21 Claims, 3 Drawing Sheets

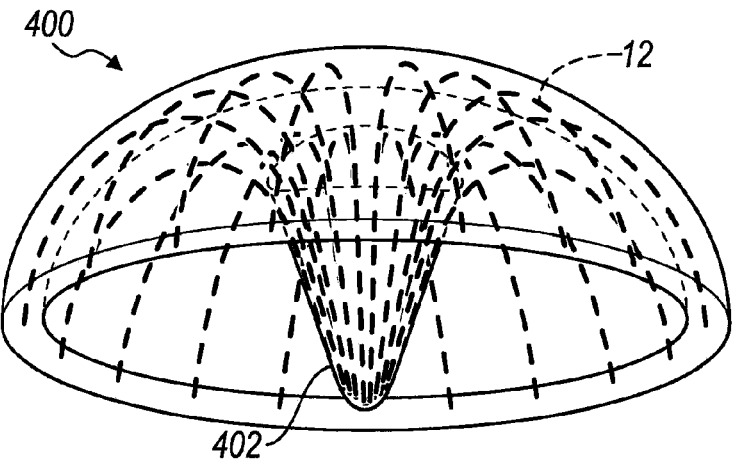
FIG. 6
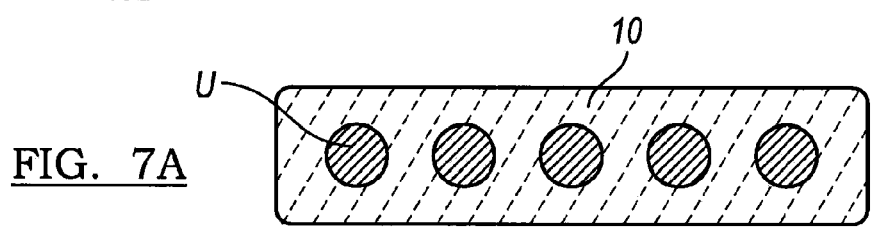
FIG. 7A
FIG. 7B
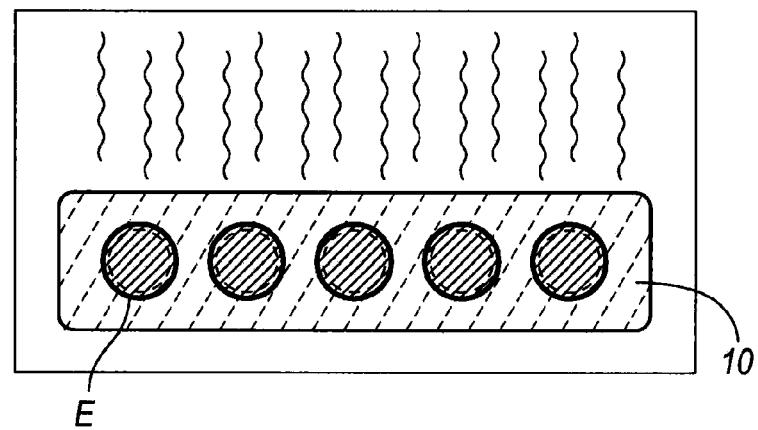
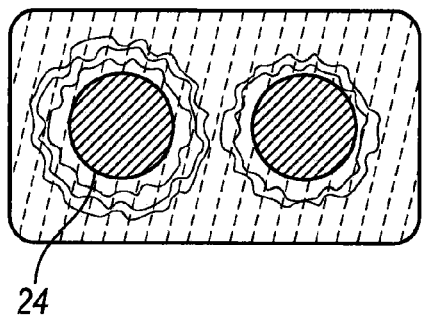
FIG. 8A
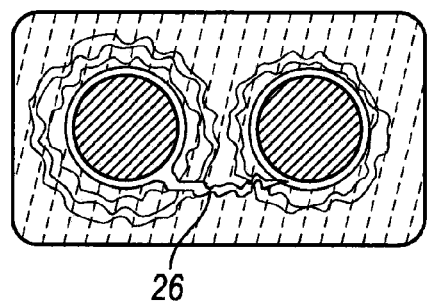
FIG. 8B

REINFORCED MEDICAL IMPLANTS

The present disclosure relates to reinforced medical implants. More particularly, the present teachings relate to ceramic implants having a metal wire embedded therein.

In various orthopedic procedures using an implant having an articulating surface, a major concern is the selection of materials to increase the longevity of the implant while also providing appropriately sized and mated articulating surfaces. The articulating surfaces can be made of a variety of materials, for examples, ceramics, metals, and high molecular weight polymers. The articulating surfaces can be highly polished or otherwise treated to provide low friction articulation to allow the surfaces to smoothly glide past each other to provide fluid and "natural" movement to the joint.

In hip arthroplasty, the hip implants are designed such that the femoral head region of the implant fits snugly in the acetabular cup. The femoral head region and the inner region acetabular cup region often have similar diameters. For example, the articulating surface or inner region of the acetabular cup can be about 38 millimeters to mate with a femoral head having a diameter of about 38 millimeters. The size match allows for smooth articulation and minimizes chances of femoral head slippage. The acetabular cup includes an inner articulating surface which is housed within a larger outer shell. The outer shell is sized to fit within the pelvic socket and provides load bearing to the region.

Acetabular shells with the 38 millimeter inner articulating surface can be attached to an outer shell having a diameter of approximately 70 millimeters or greater. The larger outer shell requires that a larger incision be made at the implant site to accommodate the acetabular cup implant. This may require that an unnecessarily large region of the bone be resected to provide a receptacle for the large outer shell, even if the surrounding bone is healthy. The larger incision and large resected region of the pelvic socket may increase recovery time and may impact patient response to physical therapy. Simply providing smaller implants by reducing the sizes of the acetabular cup components may not provide adequate attachment and fit into the pelvic socket. The smaller acetabular implants may not provide a sufficient articulating surface for a larger sized femoral head that is necessary to reduce or eliminate dislocation. It may be desirable to minimize the size of the implant without sacrificing load-bearing abilities or articulation of the implant.

Depending on the material used in the implant, the durability and load bearing capabilities of the material are proportional to the size or thickness of the material within the implant. For example, ceramic is often desirable as a part of one or both of the articulating surfaces due to the long wear characteristics, reduction in wear debris, high hardness, and low coefficient of friction. The longevity of ceramic materials is beneficial as they may lengthen the amount of time required before revision surgery on the implant or in certain advanced age patients, they may significantly reduce the chance that a revision or replacement surgery will have to be performed in the later years of life. Recent advancements in ceramics have lead to the development and implementation of ceramic-on-ceramic articulating surfaces in implants which exploit the beneficial ceramic characteristics. Even with these benefits, the ceramic must be of a sufficient thickness to prevent stresses or cracks in the ceramic which can propagate.

To increase the strength of ceramics, research has focused on optimizing a combination of fibers or fillers within the ceramic body or using powdered materials to reinforce the ceramic. These types of reinforcements are akin to composites because of the distribution of the materials and the homogeneity of the materials within the ceramic matrix. The reinforcements are designed to increase the amount of energy required to cause a fracture or crack in the ceramic, also known as the fracture energy of the ceramic. Example reinforcing materials include polymers, metals, and different ceramics. Differences between the properties of the metal or other reinforcing material and the ceramic matrix, such as the coefficient of thermal expansion, heat stability, etc., have made it difficult to provide an optimal composite material which utilizes the benefits of the reinforcing material, without making the ceramic more brittle. Moreover, use of metal powders of filings can assist in minimizing crack propagation, but these composites may not prevent "burst" failure.

Accordingly, there is a need to provide an implant to minimize the size of the orthopedic implant. It is also desirable to provide an orthopedic implant which allows for appropriate articulation and load bearing. There is also a need to provide ceramic implants which have mechanisms to prevent cracks, crack propagation, and burst failure within the ceramic.

SUMMARY

In various embodiments, the present technology provides medical implants comprising a ceramic body having a shape operable for use in the implant and a plurality of solid metal wires embedded in the ceramic body. The present technology also provides methods for forming a medical implant comprising a ceramic body having a shape operable for use in the implant and a plurality of solid metal wires embedded in the ceramic body. In some embodiments, such methods comprise:

placing a plurality of metal wires in a mold;

covering at least a region of the metal wires with a ceramic material; and compacting the metal wires and the ceramic material in the mold to form a green body.

In some embodiments, methods of preparing a metal implant having a plurality of solid metal wires embedded therein comprise:

forming a green body comprising a plurality of polymer wires, at least a portion of which is covered with a ceramic material;

heating the green body so as to remove the plurality of polymer wires and form a ceramic body having a plurality of channels;

filling the plurality of channels with a metal powder; and sintering the ceramic body to form the solid metal wires from the metal powder.

In various embodiments, methods are provided for securing an articulating medical implant to an implant site, such methods comprising:

providing the articulating medical implant comprising:

a ceramic body having a shape operable for use in the implant; and a plurality of solid metal wires embedded in the ceramic body;

where a first region of the metal wires is contained inside of the ceramic body to provide an articulating surface and a second region of metal wires extends outside of the ceramic body to provide a porous matrix on a non-articulating side of the implant; and attaching the non-articulating side of the implant to bone.

DRAWINGS

The drawings described herein are for illustration purposes only and are not intended to limit the scope of the present disclosure in any way.

FIG. 6 depicts a Copeland shoulder implant according to various embodiments;

FIGS. 7A through 7B depict a process of forming a ceramic implant according to various embodiments; and FIG. 8 depicts a toughening mechanism preventing a fracture through a ceramic implant according to various embodiments.

Figure 1:
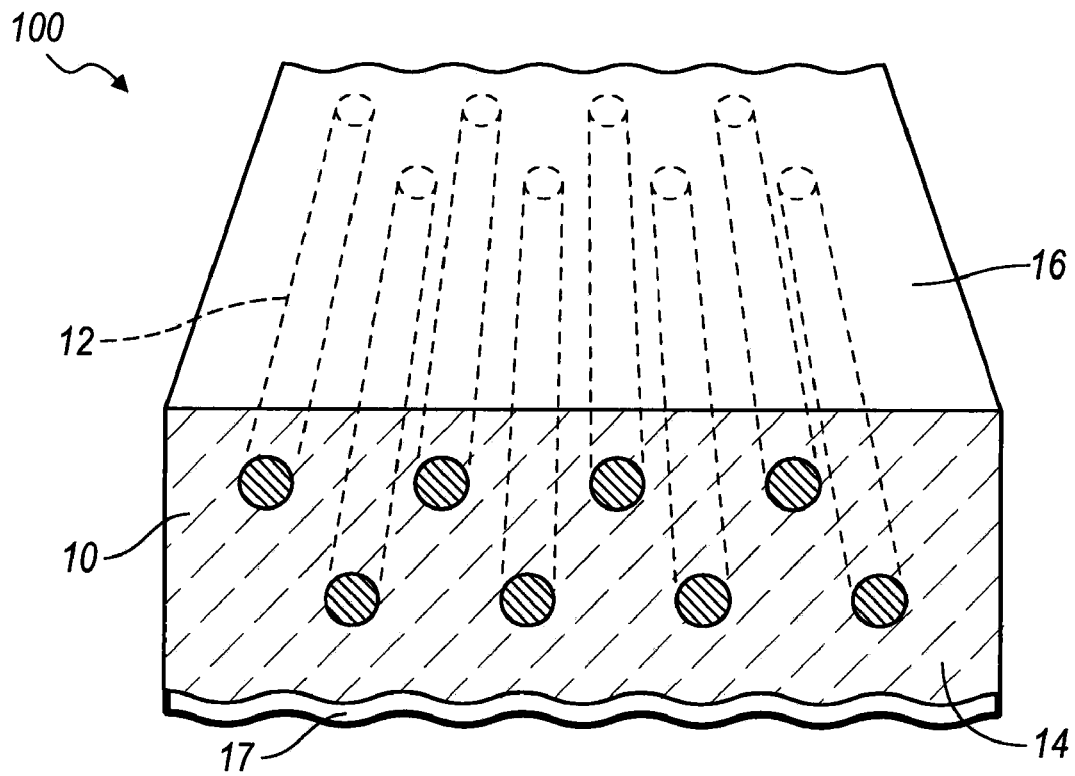
FIG. 1 depicts a cross section view of a ceramic implant according to various embodiments.
Figure 2:
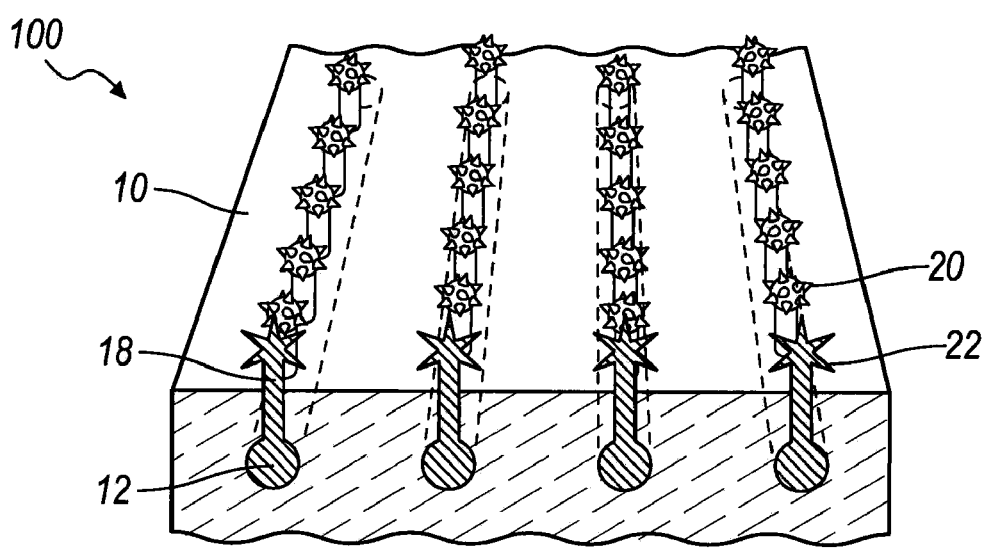
FIG. 2 depicts the bone engaging surface features of a ceramic implant according to various embodiments.
Figure 3:
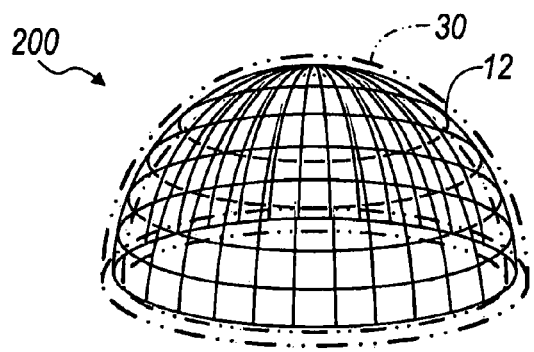
FIG. 3 depicts an acetabular cup having a wire mesh reinforcing element according to various embodiments.

It should be noted that the figures set forth herein are intended to exemplify the general characteristics of devices, materials and methods among those of this technology, for the purpose of the description of such embodiments herein. These figures may not precisely reflect the characteristics of any given embodiment, and are not necessarily intended to define or limit specific embodiments within the scope of this technology.

DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") used herein are intended only for general organization of topics within the disclosure of the teachings, and are not intended to limit the disclosure of the teachings or any aspect thereof. In particular, subject matter disclosed in the "Introduction" may include aspects within the scope of the novel technology, and may not constitute a recitation of prior art. Subject matter disclosed in the "Summary" is not an exhaustive or complete disclosure of the entire scope of this technology or any embodiments thereof. Classification or discussion of a material within a section of this specification as having a particular utility (e.g., as being a "bone ingrowth promoting agent" component) is made for convenience, and no inference should be drawn that the material must necessarily or solely function in accordance with its classification herein when it is used in any embodiments of the present technology.

The citation of references herein and during prosecution of this application does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations the stated of features. Specific examples are provided for illustrative purposes of how to make and use the devices and methods of this technology and, unless explicitly stated otherwise, are not intended to be a representation that given embodiments have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of these teachings. The terms "a" and "an" mean at least one. Also, all compositional percentages are by weight of the total composition, unless otherwise specified.

The present technology provides medical implants comprising a ceramic and plurality of embedded solid metal wires. For ease of discussion FIGS. 1 through 8 depict representative medical implants 100. The medical implants 100 include a ceramic body 10 having a shape operable for use in the implant and a plurality of solid metal wires 12 embedded in the ceramic body. The ceramic body 10 has an increased strength due to the presence of the metal wires 12. The metal wires 12 reinforce the ceramic, increase the distribution of stresses in the ceramic body 10, and prevent crack propagation through the ceramic body 10. It is understood, however, that the present technology encompasses a wide variety of implants, used for a wide variety of therapeutic and cosmetic applications, in human or other animal subjects. The specific devices and materials used must, accordingly, be biomedically acceptable. As used herein, such a "biomedically acceptable" component is one that is suitable for use with humans and/or animals without undue adverse side effects (such as toxicity, irritation, and allergic response) commensurate with a reasonable benefit/risk ratio.

The ceramic body 10 is made of any suitable ceramic material. Ceramic materials include inorganic, non-metallic materials that are processed or consolidated at a high temperature. In various embodiments ceramic materials include oxides, nitrides, borides, carbides, suicides, and sulfides. More specifically ceramics useful herein include titanium oxide, titanium dioxide, alumina ceramics, zirconia ceramics, stabilized zircornia, silicon carbide, dopants thereof, and combinations thereof. In some embodiments, the ceramic is aluminum oxide.

The ceramic body 10 has a shape operable as a medical implant for an animal subject. The medical implant 100 can be an orthopedic implant, for example, an acetabular cup 200, a knee implant such a as a condyle implant 300, a shoulder implant such as a Copeland shoulder implant 400, a spinal implant, bone fixation device, bone plate, spinal rods, rod connectors, femoral resurfacing systems such as ReCap™, marketed by Biomet, Inc. of Warsaw, Ind., USA, and the like. Exemplary and non-limiting orthopedic implants containing the metal wire reinforcement 12 are shown in FIGS. 3 through 7. With respect to FIGS. 1 and 2, the medical implant 100 can also be a custom made shape or a generic shape for filing in a bone defect caused by surgical intervention or disease. Although portions of the description may detail a particular type of medical implant 100, it is understood that the guidelines and teachings are applicable to any of the implants depicted or listed herein.

The plurality of metal wires 12 has a form selected from a mesh, a fibrous web, a coil, and combinations thereof. The term "wires" as used herein is not intended to be limiting with respect to form, shape or process, and includes wires and wire-like bodies formed before use in making a ceramic body, as well as wires and wire-like bodies formed in situ during formation of a ceramic body. The metal wires 12 can form a single and continuous piece. In various embodiments, the metal wires 12 are arranged in a form similar to a mat. The metal wires 12 can have a cross section shape such as regular shapes, an I-beam, and combinations thereof. Regular shapes include those such as circles, squares, triangles, and the like. It is understood that the cross section shape can also be a free-form or irregular shape.

The metal wires 12 are preferably biocompatible and non-reactive with the ceramic body 10 materials. In various embodiments, the metal wires 12 comprise metals including cobalt-chrome-molybdenum, cobalt, molybdenum, titanium, tantalum, tungsten, gold, platinum, alloys thereof, and combinations thereof. In some embodiments, the metal wires 12 comprise a composite material comprising metals and an additional material such as a polymer, glass, etc. In various embodiments, the specific composition of types of metal materials useful for reinforcing the ceramic is selected using such parameters as the chemical compatibility between the metal and the ceramic, the coefficient of thermal expansion (CTE) between the ceramic and the metal, and the respective biocompatibility and wear resistance properties of both the ceramic and the metal.

As exemplified in FIG. 1, in various embodiments the metal wires 12 are contained entirely in the ceramic body 10 between a first side 14 of the ceramic body 10 and a second side 16 of the ceramic body 10. An optional metal coating layer 17 can also be coated on a first side 14, as shown in FIG. 1. Located at interface between a perimeter of the metal wire reinforcement and the adjacent ceramic body materials are compressive stress lines. The stress lines result from the ceramic exerting pressure on the metal wire and the metal wire exerting pressure back onto the ceramic, as detailed later herein. The reinforcing metal wire 12 prevents crack propagation in the ceramic which, if not reinforced, can lead to burst failure of the implant.

Referring to FIGS. 3 through 6, the arrangement of the metal wires 12 in the ceramic body 10 can be directed by the shape of the implant. The acetabular cup 200 shown in FIG. 3 contains a series of longitudinal and lateral metal wires 12 used to form the support matrix. The combination of longitudinal and lateral metal wires 12 provide enhanced strength to the implant at a series of angles along the hemisphere of the acetabular cup. For example, the uppermost region (region having the smallest cross-sectional diameter) of the acetabular cup has more closely spaced metal reinforcement than the lower region (region having the largest cross-sectional diameter) of the acetabular cup. The lateral and/or longitudinal metal wires 12 can be provided as a single wire or two separate wires. In still other embodiments, each of the lateral or longitudinal lines can be a separate metal wire 12 or several wires 12.

Figure 4A:
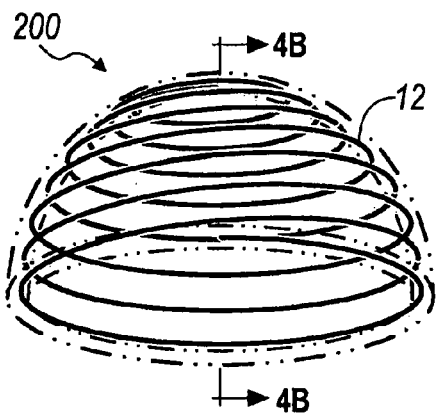
FIGS. 4A and 4B depict an acetabular cup having an I-beam wire mesh reinforcing element according to various embodiments.
Figure 4B:
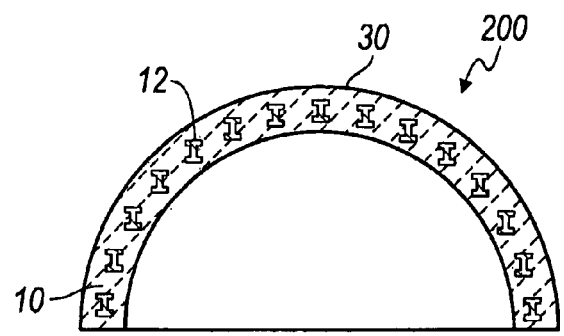

The acetabular cup 200 shown in FIGS. 4A and 4B contains a coil or a series of loops of metal wires 12, where the diameter of each loop of the metal wire coil progressively decreases with the decreasing cross-sectional diameter of the acetabular cup 200. The metal wires 12 of the coil can be evenly spaced to provide even reinforcement to the ceramic body 10 or the metal wires can be unequally spaced to provide greater reinforcement to the upper region and/or the lower region of the acetabular cup.

In various embodiments, the use of a wire reinforcement, such an I-beam wire 12 exemplified in FIG. 4B, provides compressive stress, load-bearing, and structure retention to prevent crack propagation and burst failure by absorbing and distributing the loads placed on the ceramic material in both the vertical and horizontal directions in accords with the structure of the I-beam. The I-beam metal wire 12 coil in the acetabular cup 200 follows the decreasing diameter of the hemispherical acetabular cup 200, and the load-bearing and strength enhancing characteristics of the I-beam shape are exploited to their maximum.

FIG. 6 depicts an embodiment where the metal wire 12 form is used as a portion of structural or attachment member of the Copeland shoulder 400. The metal wire 12 follows the dome contour of the Copeland shoulder and continues downwards to form a region of the attaching stem 402 of the implant.

In addition to embodiments where the metal wire 12 is covered on all opposing sides by the ceramic body 10, additional embodiments are contemplated where a first region of the metal wire reinforcement is contained inside of the ceramic body 10 at the first side 14 of the ceramic body and a second region of metal wire reinforcement or projections 18 extends outside of the ceramic body 10 at the second side 16 of the ceramic body 10. The region of the projections 18 extending outside of the ceramic body 10 can serve as a matrix for bone ingrowth. This matrix can be porous, reticulated, weaved, contain gaps or spaces between the projections, or otherwise provide a region in which bone can grow into and further secure the implant. In still further embodiments, the projections 18 can extend from both sides 14, 16 of the ceramic body 10. Alternating projection patterns can also be advantageously incorporated into the ceramic body 10.

Figure 5:
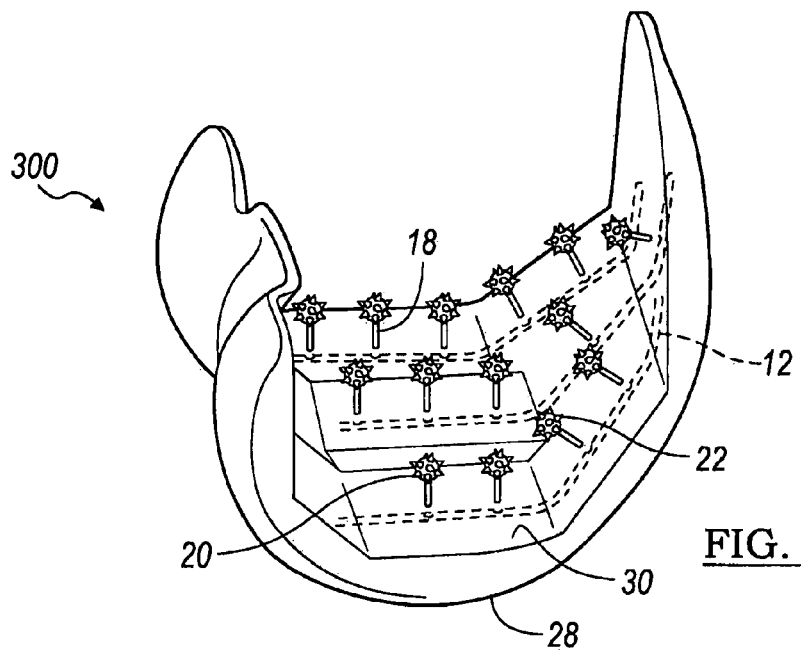
FIG. 5 depicts a condyle implant according to various embodiments.

The projections 18 can be a region of the metal wire 12 or the projections 18 can be additional surface features 20 on the wire 12. Exemplary surface features 20 are spikes, barbs, teeth, or similar tissue engaging protrusions. As depicted, the surface features are barbs 22. The projections 18 from the metal wire 12 or from the additional surface features 20 can be used as substrate for porous plasma spray, for bone engagement, or for a porous matrix for the ingrowth of bone. For example, in embodiments where a wire mesh or wool is employed, the new bone tissue can grow into the mesh. As shown in FIG. 5, the projections 18 can be used to affix the knee implant to a resected femur.

Referring to FIGS. 7A through 8B, the present technology also provides methods for forming a medical implant 100. Forming the wire reinforced ceramic generally requires material selection and preparation, green forming, and densification of the green into the final implant 100. Optional steps to expedite formation of the implant 100 or increase strength thereof or to accommodate for various surface features of the implant 100 can be conducted at various points during the process. Also various finishing steps can be employed. It is understood that any of the below processes can be performed in any order or combination and the formation process is not limited to those specifically provided here.

The ceramic material can be provided in dry powder form or the ceramic powder can be in a wet or slurry form. In various embodiments, the ceramic has been crushed, milled, pulverized, or ground into the appropriate size. The ceramic powder can have a particle size of from about 0.1 to about 25 micrometers. In various embodiments, the ceramic powder can have a particle size of less than about 5 micrometers or less than about 1 micrometer. The ceramic powder should be substantially free from impurities that could interfere with the forming and consolidation processes. Appropriately sized and purified particles facilitate successful completion of the processing steps and can prevent creating a ceramic material that may be susceptible to a crack.

The ceramic starting materials can also include binders and deflocculating agents, known in the art to facilitate formation of the ceramic. Additional steps such as water removal or calcinations can also be performed on the ceramic.

The ceramic powder and the metal wire are formed into useful shapes using a green-forming process. The green or the preliminary piece has an intact and cohesive structure, but lacks the density and integrity of the final structure. The green-forming process used can be chosen based on the particular ceramic and metal wire chosen, whether the wire is pre-formed or formed in situ, the implant shape desired, the biomechanical properties desired, and the load-bearing needs of the implant area. Green-forming processes suitable for embodiments of the present invention, include, but are not limited to casting, die pressing, and isostatic pressing, which are all well known in the art.

In embodiments where the ceramic mixture contains a liquid component, slip casting or drain casting can be used to form the implant. Slip casting is a green-forming process where a slip or a wet mixture containing a ceramic powder is molded. The slip is poured into a porous mold. The pores in the mold cause water or other liquid in the slip to draw out of the slip and form a solid layer of the ceramic in the mold. Additional slip can be poured into the mold until the desired thickness of the ceramic is achieved.

The metal wire 12 reinforcement can be placed into the mold at any point during the slip process, or formed in situ. In various embodiments, the wire is preformed. It may be desirable to place the metal wire 12 reinforcement onto a layer of the slip such that the metal wire 12 reinforcement will be aligned in the ceramic at an equal distance from the upper surface 14 and lower surface 16 of the implant 100. The slip process is also advantageous because the openness of the mold and the ability to control the drying process allows for a variety of types of metal wire 12 reinforcements to be placed in the ceramic. The slip is partially dried in the mold to cause the final ceramic implant 100 to shrink away from the inside edges of the mold.

An extension of slip casting, known as pressure casting can also be used. Pressure is applied to the slip to expedite removal of the liquid material from the ceramic. The pressure forms a more compacted implant 100. Either slip or pressure casting are useful because of the broad types of shapes which can be made. The mold can be shaped, for example, as an acetabular cup. The arcuate surface of the mold and the thickness of the ceramic therein can be controlled by the addition of the slip and waiting for capillary action of the porous mold.

In embodiments where the ceramic mixture is dry (less than about 5% water or liquid content), powder pressing can be used. Powder pressing includes die pressing and cold isostatic pressing. In die pressing, the ceramic mixture is placed into a steel or tungsten carbide die and internal punches are used to apply pressure to the die. The metal wire 12 reinforcement can be placed in the die prior to placing the ceramic mixture or after the ceramic mixture is placed in the die. The green mixture is then compacted under pressure. Generally with die pressing, the compacted piece needs to be shaved, ground, or otherwise shaped into a desirable shape.

The die pressing technique is advantageous for simple shapes such as a flat or minimally arcuate or curved surface such as a cranial plate, for example.

A preferred powder pressing technique is cold isostatic pressing. Cold isostatic pressing allows for the formation of complex shapes and highly arcuate shapes such as an acetabular cup. Cold isostatic pressing is conducted at a temperature of less than about 200° C. and is generally conducted in a flexible mold.

Optionally after the green forming, a drying or organic removal step can be performed. The organic binder or other material(s) is removed by drying the material in a low temperature oven, for example, to remove residual solvents, dispersants, or binders.

As shown in FIG. 7A and 7B, the densification of the green can be conducted using processes such as hot pressing, hot isostatic pressing, and sintering. The densification removes undesired porosity from the implant and causes the metal and the ceramic material to be further compressed to or against the other material.

A useful densification technique is sintering. Sintering is conducted in a vacuum and the green compact is subjected to high pressure. The pressure can be uniaxial, multiaxial, or isostatic. Particularly, the sintering temperature is selected such that it is sufficient to cause a re-arranging and interlocking of the crystalline structure of the ceramic materials. In various embodiments, it is desirable to increase the sintering temperature to a temperature sufficient to deform the metal wire reinforcement. Deforming includes partial melting and complete liquefaction of the metal to a molten state.

In various embodiments, the sintering is conducted at a temperature which exploits the thermal mismatch between the metal wire reinforcement and the ceramic material. When the temperature is above the sintering temperature of the metal, the unexpanded metal wire U expands within the ceramic matrix. This causes the metal wire to increase to its expanded size E. This temperature can be below, equal to or above the sintering temperature of the ceramic. When the ceramic and metal wire are sintered, the metal wire expands while the ceramic is compressed. This causes the ceramic to squeeze against the perimeter of the metal wire 12 while the metal attempts to press back onto the ceramic material. The force and counter force from the metal and the ceramic cause compressive stress in the ceramic. The compressive stresses prevent cracks from spreading in the ceramic and form a hard and durable implant.

In various embodiments, the sintering can include a thermal cycling or a system of temperature increases and decreases in the system to provide the metal-ceramic interface. The temperature is increased to a first holding temperature and maintained at that temperature for a period of 1 hour to 8 hours. The temperature is then increased to a second, higher holding temperature for a period of 1 hour to 10 hours. The temperature is decreased to from the second temperature to a third holding temperature at a steady cooling rate. The temperature is maintained at the third holding temperature for a shorter duration of time, generally less than 1 hour. The heating element or oven is turned off and the part is allowed to cool in the furnace until the implant reaches an appropriate handling temperature or room temperature. In various embodiments, the furnace could be programmed to gradually lower the temperature.

If the expansion of the metal is sufficient, a toughening mechanism 24 is formed in the implant 100. In various embodiments, the toughening mechanism 24 is a space or air pocket or air gap 26 formed between the metal and the surrounding ceramic. The air gap 26 provides an interior air barrier between at least a region of the metal wire 12 and a region of the surrounding ceramic material. The toughening mechanism prevents a crack from spreading in the final implant 100. For example, if the implant 100 is impacted to cause a crack 26, the stress distribution will stop once the crack 26 reaches the air gap 26 as the stress is no longer being continually distributed through solid matter. The crack 26 requires a substrate through which to propagate.

As another example, the sintering temperature and pressure can also be such that a ceramic-metal interface is formed due to melting of the metal wire. The molten metal is integrated with the ceramic. In such embodiments, it is desirable that the metal wire is made of an inert metal to prevent reaction of the metal with the ceramic.

In hot pressing, pressure is applied to the powder compact in a die at an elevated temperature. Unlike cold isostatic pressing, the compaction used in hot pressing is carried out at elevated temperatures, or temperatures above about 200° C. Hot isostatic pressing can be used to further densify materials that have been sintered in a process called post-hot isostatic pressing.

In various embodiments, the solid metal wire reinforcements can be formed using a metal injection molding technique. Forming the medical implant 100 by implementing the metal injection molding technique may be similar to the techniques described above herein, but instead of embedding the metal wire into the ceramic material, a metal is "backfilled" into a plurality of channels formed in the ceramic body.

In some such embodiments, the metal wires are formed in situ, during production of the ceramic body. In various embodiments, a green body is formed comprising a plurality of polymer wires, at least a portion of which is covered with a ceramic material. The polymer may be any of a variety of materials that are operable to degrade, in whole or in part, during heating or other processing of the ceramic body so as to form voids (i.e., channels) in the body. In one embodiment, the polymer is nylon. The polymer wires can be in the form of discrete wires or the polymer wires can be in the form of a mesh, fibrous web, or a coil. Any of the shapes mentioned above herein including I-beam shapes are suitable for the cross section of the polymer wires. The polymer wires can be sized to be embedded in the ceramic material or the polymer wires can be sized and/or oriented such that the wires extend beyond the surface of the ceramic material. These polymer wire extensions can be used to facilitate filling the metal into the ceramic body, as detailed later herein, or can be used to facilitate formation of features on the implant, such as the post of the Copeland shoulder.

In some embodiments, a plurality of polymer wires is placed into a mold during formation of a green body. At least a region of the polymer wires is covered with a ceramic material and any additives, such as those listed above herein. The polymer wires and the ceramic material may then be compacted to form the green body. The green body is then heated so as to destroy or otherwise remove the polymer wires, so as to form a plurality of hollow channels in the pattern of the polymer wires in the compacted green body. In some embodiments, the heating temperature is selected so as to melt the polymer wires and the melted polymer can be poured out of the compacted green body, or the temperature can be selected to substantially burn off the polymer wires. In some embodiments, the heating to remove the wires may be performed at a temperature to sinter the ceramic body. In some embodiments, the ceramic body is sintered during a subsequent step, such as during the formation of the solid metal wires in the channels, as further described below.

The channels formed due to removing the polymer wires can be interconnected or discrete channels so long as the channels are at least partially accessible for incorporation of the metal. For example, in embodiments where regions of the polymer wire extended beyond surface of the ceramic material, those regions can serve as inlets for the metal powder. The metal powder is then deposited into the channels. In some embodiments, this is performed by a metal injection process. The green body with the metal powder is then heated (in some embodiments, sintered) at a temperature above the melting point of the metal such that upon cooling, the metal powder forms a solid, continuous metal wire.

Additional processing steps can be performed on either the green body or the sintered implant. The green body or the sintered implant can be machined to form an appropriate implant shape (i.e., a Copeland shoulder). Other suitable formation steps include, but are not limited to, polishing, coating with a protective sealant or barrier layer, or coating with a bone ingrowth promoting agent.

A "bone ingrowth promoting agent" is any material that is able to increase integration of healthy bone tissue into the medical implant, facilitate repair of an unhealthy or damaged tissue, minimize infection at the implant site, and/or serve as a preventative measure against disease or defects in healthy or damaged tissue. Bone ingrowth promoting agents include, but are not limited to, calcium containing materials, nutrient factors, bone morphogenic proteins, growth factors, antimicrobials, anti-inflammatory agents, blood products and mixtures thereof. (See, e.g., U.S. Pat. No. 6,180,606, Chen, et al., issued Jan. 30, 2001, incorporated by reference.) The bone ingrowth promoting agents also include the biomedically acceptable salts, isomers, esters, ethers and other derivatives of the above compounds.

"Calcium containing" materials include hydroxyapatite, monobasic, dibasic and tribasic calcium phosphates, calcium aluminates, calcium containing ceramics, porous calcium containing ceramic particles and amorphous calcium phosphate.

As used herein, a "nutrient factor" is a compound or mixture of compounds used to sustain metabolic activities or used to promote normal physiologic function or optimal health. Nutrient factors include vitamins, hormones, amino acids, carbohydrates or derivatives thereof, fats or derivatives thereof, alcohols or derivatives thereof, inorganic salts and trace elements, and mixtures thereof.

As used herein, "bone morphogenic proteins" are the proteins involved in induction of bone and cartilage formation. Bone morphogenic proteins include BMP-2, BMP-2a, BMP-4, BMP-5, BMP-6, BMP-7 and BMP-8.

As used herein, a "growth factor" is a substance that is operable to increase the size of a living being or any of its parts or to stimulate cell growth. Growth factors include Transforming Growth Factor-beta (TGF-β), Transforming Growth Factor-alpha (TGF-∝), Epidermal Growth Factor (EGF), Insulin-like Growth Factor-I or II, Interleukin-I, Interferon, Tumor Necrosis Factor, Fibroblast Growth Factor (FGF), Platelet Derived Growth Factor (PDGF) and Nerve Growth Factor (NGF).

As used herein, "anti-inflammatories" include steroidal and non-steroidal anti-inflammatory agents.

As used herein, a "blood product" is a product, any component of which is derived from blood. Blood products include whole blood and blood fractions, such as plasma, blood cells, blood factors, blood related proteins, unspecialized cells such as stem cells (including adipose derived stem cells), or specialized cells, e.g., types of leukocytes such as lymphocytes and dendritic cells.

Other suitable materials may include inorganic materials, metals, such as mesh titanium or titanium alloy, amino acids, gelatin, collagen, naturally occurring or synthetic therapeutic drugs, proteins and enzymes.

A method of securing an articulating medical implant to an implant site is also provided. The method includes providing the articulating medical implant, such as the acetabular cup 200 or condyle implant 300. The articulating medical implant includes a ceramic body having a shape operable as an implant and a plurality of metal wires 12 embedded in the ceramic body 10.

Referring to FIGS. 4B and 6, a first region of the metal wire reinforcement is contained inside of the ceramic body 10 to provide an articulating surface 28 and a second region of metal wire reinforcement extends outside of the ceramic body to provide a porous matrix on a non-articulating side or surface 30 of the implant. The non-articulating surface 30 of the implant attaches to bone. This is particularly advantageous when the non-articulating surface 30 of the implant is a porous mesh or web such as those described earlier herein. The porous mesh or web allow for the implant to be secured into the defect site and maintained by natural tissue. The ingrowth of the natural tissue facilitates the longevity and/or permanency of the implant.

The devices, materials and methods of this technology are further illustrated by the following non-limiting examples.

EXAMPLE 1

A slurry is prepared of an aluminum oxide powder and a binder system. The particles have a diameter of less than 5 microns. A mesh of tantalum wire is fabricated into a hemispherical shaped pad and the pad is placed in the mold cavity resembling an acetabular shell. The slurry is poured in the cavity with the metal wire pad. The compacted ceramic body with the metallic reinforcement is extracted from a flexible mold and dried. The green compact is sintered according to the following sintering temperature profile. The green compact is placed in an oven at room temperature. The temperature is increased to 175° C. at a rate of 5° C./minute. The green compact is held in the oven at 175° C. for 4 hours. The temperature in the oven is ramped to 1650° C. at 5° C./minute. The temperature is held at 1650° C. at 8 hours. The temperature is decreased to 600° C. at 5° C./minute. The temperature is held at 600° C. for 30 minutes. The oven is turned off and the part is allowed to cool in the furnace until it reaches an appropriate handling temperature or room temperature.

EXAMPLE 2

A slurry is prepared of silicon nitride powder and a binder system with additives of either magnesium oxide (MgO) or yttrium oxide ($Y_2O_3$), which can be used separately, in combination or with aluminum oxide ($Al_2O_3$). The additives promote liquid phase sintering. The ceramic powder particle size is less than 10 micrometers. The slurry is placed in a knee-component shaped mold. A nylon polymeric mesh is placed in the mold so that the ends of the polymer will ultimately reside outside the body of the cast ceramic. The mold is cast with the prepared slurry and dried using an oven.

The dried system is sintered according to the following sintering temperature profile. The green compact is placed in an oven at room temperature. The temperature is increased to 200° C. at a rate of 2° C./minute in air environment. The green compact is held in the oven at 200° C. for 2 hours and the temperature is increased to 400° C. at 2° C./minute and held at this temperature for 2 hours. After the polymeric mesh has burnt out, the air is evacuated from the oven and replaced with nitrogen. The nitrogen pressure is built up to almost 10 MPa to prevent the dissociation of silicon nitride. Under this high pressure nitrogen atmosphere, the temperature in the oven is ramped to 1850° C. at 2° C./minute and held at 1850° C. for 2 to 4 hours. The temperature is then cycled as follows. The temperature is decreased to 1200° C. at 2° C./minute and held at this temperature for 1 hour, then decreased to 800° C. at 2° C./minute and held at this temperature for 1 hour, and then decreased to 600° C. at 2° C./minute and held at this temperature for 1 hour. Finally, the oven is turned off and the part is allowed to cool in the furnace until it reaches an appropriate handling temperature or room temperature. When the part is removed from the furnace, the part is a dense silicon nitride system with open channels once occupied by the nylon wires. The dense ceramic is placed in another mold cavity and infiltrated with slurry of Ti6Al4V powder and binder, commonly practiced in Metal Injection Molding. This system is placed in another furnace and gradually heated to burn off the binder in air and then heated at 1300° C. for 2 hours in vacuum to sinter the metal. This operation results in a system where the ceramic is infiltrated with sintered titanium alloy.

EXAMPLE 3

The cavity walls of a flexible mold are pre-coated with tantalum particles that are in excess of 2 millimeters in diameter using a polymeric binder. The mold cavity is filled at strategic locations with pads of tantalum mesh. The locations are pre-identified as regions with inherent weakness. Magnesium oxide stabilized zirconia powder having a particle size of less than 1 micrometer is poured in the cavity. The filled mold is connected to a vacuum source and air is removed to pressures less than 1 atmosphere. The mold is continuously vibrated to help settle the powder in the pores of the metal pads and between the metal particles on the mold walls. The system is placed in a cold iso-static system and pressurized to pressures in excess of 69 mega pascals. The compact is extracted from the mold and placed in a vacuum furnace where it is sintered under vacuum of less than 1 atmosphere. The temperature in the vacuum furnace is cycled as follows. The temperature is heated to 300° C. at 2° C./minute and then heated to 600° C. at 2° C./minute and held at that temperature for 30 minutes. The temperature is heated to 900° C. at 2° C./minute and held for 30 minutes, heated to 1725° C. at 1° C./minute and held at this temperature for 2 hours. The temperature is then cooled in a cycle. The temperature is reduced to 1400° C. at 10 to 15° C./minute, cooled to 1150° C. at 2 to 5° C./minute and cooled to 775° C. at 3° C./minute. The temperature is then reheated to 1100° C. at 2° C./minute and held at 1100° C. for 2 hours. Finally, the furnace is turned off and the part is cooled in furnace. The sintered device is then placed in a plasma spray system and the composite surface (tantalum with magnesium stabilized zirconia) is plasma sprayed with Ti6Al4V powder to generate a rough osteointegrating surface. The surface with no metal (the articulating surface) is polished to a roughness of less than 0.1 micron Ra to provide the articulating surface.

EXAMPLE 4

Porous tantalum pads are fabricated and placed in a knee femoral component such that the tantalum pads are in contact with the bone side of the condyle. Aluminum oxide powder having a particle size of less than 1 micron is poured in a femoral component flexible mold coating the tantalum pad. The filled mold is pressurized above 20000 psi and then extracted from the mold to form a green part. This green part is partially consolidated at temperatures between 600 to 900° C. in a vacuum furnace. The partially consolidated part is machined to resemble a knee component with texture on the bone side and expose the tantalum pads on the bone side of the condyles. The partially consolidated part is then returned to the vacuum furnace and sintered using the following thermal profile. The temperature is increased to 150° C. at a rate of 2° C./minute and held for 2 hours. The temperature is ramped to 1550° C. at 1° C./minute and held for 2 hours, after which the temperature is decreased to 900° C. at 1° C./minute. The temperature is then cooled to 600° C. at 1° C./minute, where it is held for 30 minutes. The oven is turned off and the part is allowed to cool in the furnace until it reaches an appropriate handling temperature or room temperature.

The examples and other embodiments described herein are exemplary and not intended to be limiting in describing the full scope of devices and methods of this technology. Equivalent changes, modifications and variations of specific embodiments, materials, devices and methods may be made within the scope of the present technology, with substantially similar results.

What is claimed is:

1. A medical implant, comprising:
a ceramic body having a shape operable for use in the implant; and a plurality of solid metal wires embedded in the ceramic body and dispersed throughout the implant forming an internal matrix operable to minimize crack propagation, wherein each of the plurality of metal wires comprises a first region contained inside of the ceramic body and a second region extending a distance outside a first surface of the ceramic body, the plurality of wires forming a matrix of the second regions to promote bone ingrowth.

2. A medical implant according to claim 1, comprising a second surface operable as an articulating surface for the implant.

3. A medical implant according to claim 1, wherein the first surface is coated with a metallic layer.

4. A medical implant according to claim 1, wherein the ceramic body is made of a material selected from the group consisting of titanium oxide, titanium dioxide, alumina ceramics, zirconia ceramics, silicon carbide, stabilized zirconia, and mixtures thereof.

5. A medical implant according to claim 1, wherein the metal wire is non-reactive with the ceramic body.

6. A medical implant according to claim 1, wherein the metal wire comprises a metal selected from the group consisting of cobalt-chrome-molybdenum, cobalt, molybdenum, titanium, tantalum, tungsten, gold, platinum, alloys thereof, and combinations thereof.

7. A medical implant according to claim 6, wherein the metal wire comprises titanium, tungsten, or combinations thereof.

8. A medical implant according to claim 1, wherein the metal wires comprise a form selected from the group consisting of meshes, fibrous webs, coils, and combinations thereof.

9. A medical implant according to claim 8, wherein the form is a mesh.

10. A medical implant according to claim 1, wherein the second region of the wires further comprises surface features.

11. A medical implant according to claim 1, having compressive stress lines at an interface between a perimeter of the metal wire and an area of the ceramic body adjacent to the metal wire.

12. A medical implant according to claim 1, wherein the wires further comprise an attachment feature connected to a surface feature for attaching the medical implant to an implant site.

13. A medical implant according to claim 12, wherein the attachment feature is a post.

14. A medical implant according to claim 12, wherein the first region of each metal wire is proximate to the attachment feature so as to reinforce the implant in the area of the feature.

15. A medical implant according to claim 1, wherein the medical implant is selected from the group consisting of: an acetabular cup, a shoulder implant, and a knee implant.

16. A medical implant, comprising: a ceramic body comprising a ceramic material and having a shape operable for use in the implant; and a plurality of solid metal wires embedded in the ceramic material of the ceramic body and dispersed throughout the implant, wherein each of the solid metal wires comprises a first region contained inside of the ceramic material forming a support matrix operable to minimize crack propagation, and a second region comprising a projection that extends a distance outside from a first surface of the ceramic body for receiving a porous metal spray.

17. A medical implant according to claim 16, comprising a second surface operable as an articulating surface for the implant.

18. A medical implant according to claim 16, wherein the metal wires comprise a form selected from the group consisting of meshes, fibrous webs, coils, and combinations thereof.

19. A medical implant according to claim 16, wherein respective projections from the plurality of metal wires extend from opposing sides of the ceramic body.

20. A medical implant according to claim 16, wherein certain of the projections from the plurality of metal wires cooperate to provide an external matrix for bone ingrowth.

21. A medical implant according to claim 1, wherein the second region of the metal wire comprises a tissue engaging protrusion.

* * * * *

UNITED STATES PATENT AND TRADEMARK OFFICE
CERTIFICATE OF CORRECTION

| | | |
|---|---|---|
| PATENT NO. | : 8,043,382 B2 | Page 1 of 1 |
| APPLICATION NO. | : 11/712360 | |
| DATED | : October 25, 2011 | |
| INVENTOR(S) | : Mukesh Kumar et al. | |

It is certified that error appears in the above-identified patent and that said Letters Patent is hereby corrected as shown below:

In the Specifications:

Column 4, Line 50; "suicides" should be --silicides--.

Signed and Sealed this
Fourth Day of June, 2013

Teresa Stanek Rea
*Acting Director of the United States Patent and Trademark Office*